United States Patent [19]

Klingler et al.

[11] 4,245,093
[45] Jan. 13, 1981

[54] PROCESS FOR THE PRODUCTION OF BASIC SUBSTITUTED ALKYLTHEOPHYLLINE DERIVATIVES

[75] Inventors: Karl H. Klingler, Langen; Franz Hitzel, Mörfelden; Erich Bickel, Frankfurt, all of Fed. Rep. of Germany

[73] Assignee: Deutsche Gold- und Silber-Scheideanstalt vormals Roessler, Hanau, Fed. Rep. of Germany

[21] Appl. No.: 50,744

[22] Filed: Jun. 21, 1979

[30] Foreign Application Priority Data

Jun. 23, 1978 [GB] United Kingdom ............... 27707/78

[51] Int. Cl.³ .......................................... C07D 473/08
[52] U.S. Cl. ................................... 544/267; 424/253
[58] Field of Search .......................................... 544/267

[56] References Cited

U.S. PATENT DOCUMENTS 3,728,346  4/1973  Klingler ............................... 260/256

FOREIGN PATENT DOCUMENTS 1545725 12/1971 Fed. Rep. of Germany .
2136643  2/1972 Fed. Rep. of Germany .

OTHER PUBLICATIONS

Kloetzel J. Org. Chem., vol. 20, pp. 38-49, (1955).
Klingler, Arzneimittelforschung, vol. 27, pp. 4-14, (1977).

*Primary Examiner*—Nicholas S. Rizzo
*Attorney, Agent, or Firm*—Cushman, Darby & Cushman

[57] ABSTRACT

There is described a process for the production of theophylline derivatives of the formula

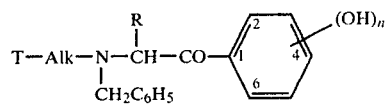

where T is the theophyllinyl-(7)-residue, Alk is a straight or branched alkylene chain having 2 to 4 carbon atoms, R is hydrogen or a methyl group, n is 1 or 2 with the proviso that two hydroxy groups of the phenyl ring cannot be in the 3,4-positions by reacting an aminoalkyltheophylline of the formula

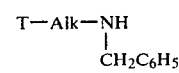

with a bromoketone of the formula

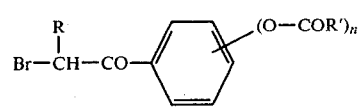

where R' is a lower alkyl group and the two —OCOR' groups of the phenyl ring cannot be in the 3,4 positions to an intermediate compound of the formula

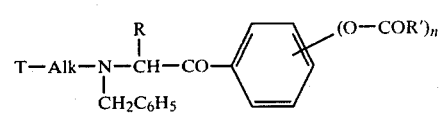

and subsequently hydrolytically splitting off the R'CO protective group wherein the bromoketone of formula III is produced free of dibromide by bromination of a ketone of the formula

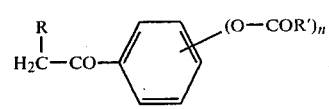

followed by treatment with a lower trialkyl phosphite.

21 Claims, No Drawings

PROCESS FOR THE PRODUCTION OF BASIC SUBSTITUTED ALKYLTHEOPHYLLINE DERIVATIVES

BACKGROUND OF THE INVENTION

Compounds of the formula

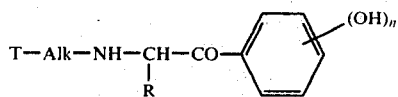
A where T is the theophyllinyl-(7)-residue, Alk is a straight or branched alkylene chain having 2 to 4 carbon atoms and R is hydrogen or a $C_1$-$C_6$ alkyl group, n is the number 1 or 2 and the phenolic OH groups and/or the basic nitrogen atom can be protected are important intermediate products for the production of pharmacologically useful compounds of the formula

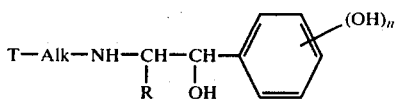
B

To produce such intermediate products of formula A it is recommended in German Pat. No. 1 545 725 to react the benzylaminoalkyl theophyllines of formula II with the halogeno ketones of formula IIIa

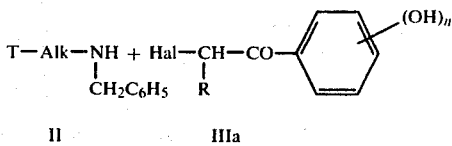

In this reaction it is frequently suitable, especially in the case where n is 2 to protect the OH groups through acyl or benzyl groups. Examples of this are described in German Offenlegungsschrift No. 2 136 643 (and related Klingler U.S. Pat. No. 3,728,346) as well as in Klingler, Arzneimettelforschung, Volume 27, pages 4–14 (1977). Thus, for example, the process given on page 13 under 4.7.1 to 4.7.3 of this publication serves to produce 7-{3-[2-(3,5-dihydroxyphenyl)-2-oxo-ethyl-benzylaminol]-propyl}-theophylline with advantage compared to the process described in Example 2 of German Offenlegungsschrift No. 1 545 725 with unprotected phenolic hydroxy groups.

The oxygen sensitivity of intermediate products of formula IIIa can be eliminated by the acetyl protective group. Besides for example the 3,5-diacetoxy-α-bromacetophenone is easily available by bromination of the commercial 3,5-diacetoxyacetophenone, while the 3,5-dihydroxy-α- chloracetophenone used in Example 2 of German Offenlegungsschrift No. 1 545 725 must be constructed in a four-step synthesis from 3,5-dihydroxybenzoic acid (see for the 2,5- isomer Koetzel, J. Org. Chem., Volume 20, pages 38–49 (1955)).

Based on the described advantages, for example, the process starting from 3,5-diacetoxyacetophenone is suited as the starting place for a commercial process of production. However, in practice upon enlargement of the amounts of the ingredients, especially on a commercial scale, there occur the following important difficulties:

1. The bromoketone obtained by bromination of the dialkanoyloxyacetophenone always contains large amounts (for example 10–20%) of more highly brominated by-products (di and tribromoketones as well as nucleus brominated products). These by-products cannot be removed in satisfactory manner.

2. The yields in the condensation of the bromoketone III obtained in impure form by the customary bromination with the amine of formula II are particularly unsatisfactory with large scale additions.

3. The thus obtained intermediate product IV in the deacylation produces a too impure product for the subsequent hydrogenation. The recrystallization required therefor is much too full of loss on a commercial scale of production.

SUMMARY OF THE INVENTION

It has now been found that the described disadvantages can be eliminated if after the bromination of the 3,5-dialkanoyloxyacetophenone V the reaction solution is post-treated with a trialkyl phosphite, e.g., a lower trialkyl phosphite. The thus isolated bromoketone is free from overbrominated ketones and in the subsequent condensation step surprisingly produces the intermediate product of formula IV in 90 to 100% yields. The deacylation likewise proceeds in over 90% yield. The product of formula I obtained thereby already is so pure that without further purification it can be added for catalytic hydrogenation wherein the oxo group reduces to the hydroxy group and the benzyl protective group on the middle nitrogen atom is split off

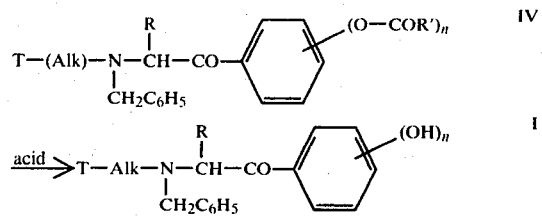

where T is the theophyllinyl-(7)-residue, Alk is a straight or branched alkylene chain having 2 to 4 carbon atoms, R is hydrogen or a methyl group, n is 1 or 2 with the proviso that two hydroxy (or two alkanoyloxy) groups of the phenyl ring cannot be in the 3,4-position and R' is a lower alkyl group.

To carry out the process of the present invention, the ketone of the formula

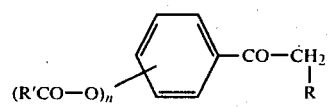
V where R is hydrogen or a methyl group and R' is a lower alkyl group (preferably with 1–4 carbon atoms) is brominated in an organic solvent in the customary manner. As solvents there can be used, for example; $C_1$-$C_4$-polyhaloalkanes (for example, polychloroalkanes), particularly $C_1$-$C_2$-dichloroalkanes, $C_1$-$C_2$-dibromoalkanes, $C_1$-$C_2$-trichloroalkanes, $C_1$-$C_2$-tetrachloroalkanes, $C_1$-$C_2$-tribromoalkanes or $C_1$-$C_2$-tetrabromoalkanes such as methylene chloride, chloroform, carbon tetrachloride, bromoform, methylene bromide, carbon tetrabromide, 1,2-dichloroethanes, 1,2- dibromoethane, 1,1,2- trichloroethane, 1,1,2-tribromoethane, 1,1,2,2-tetrachloroethane, 1,4-dichlorobutane, 1,4-dibromobutane, aromatic hydrocarbons, e.g., benzene or chlorobenzenes, e.g., monochlorobenzene, p-dichlorobenzene, or $C_1$-$C_4$-alkyl benzenes, e.g., toluene, o, m and p-xylene, ethyl benzene, butyl benzene, lower aliphatic saturated symmetrical and asymmetrical ethers with alkyl groups of 1-6 carbon atoms such as diethyl ether, dibutyl ether, dimethyl ether, methyl hexyl ether, dihexyl ether, diisopropyl ether; glacial acetic acid. Preferably there is used a bromine excess between 5 mole % and 30 mole %. The bromine either undiluted or dissolved in one of the above-mentioned solvents is dropped into the stirred solution of the ketone.

The bromine can also be led into the reaction solution in vapor form by means of a gas stream (e.g., nitrogen, $CO_2$, air). To remove the hydrogen bromide form the dropping in method of bromination in a gas stream is also recommended. There is used a temperature range of 0 to 60° C., preferably 10° to 40° C.

After the bromination there is preferably added to the reaction mixture, which produces a mixture including the corresponding mono and over brominated ketones as well as additional by-products, acetic acid, glycine or another acid with a $p_K$ value larger than 2 (for example, a $p_K$ value of 2-5 or a $p_K$ value of 2-10) and a lower trialkyl ester (preferably with alkyl groups of 1-4 carbon atoms of phosphorous acid) in an amount approximately equal to the excess bromine used and the mixture is post-stirred a short time (5 minutes to 2 hours) at 0° C. to 30° C., whereby the temperature optionally can be increased up to 40°-100° C. or up to the boiling point of the solvent used. The particular acid used is not critical so long as it has a $p_K$ value in the stated range. If addition of the acid is omitted there is likewise obtained pure monobromoketone. In this case, however, under some circumstances the yields can be somewhat lower, since then for example the original dibromoketone present is not converted into monobromoketone, but according to the Perkow reaction with the phosphite only reacts to the bromvinyl phosphate ester of formula VI

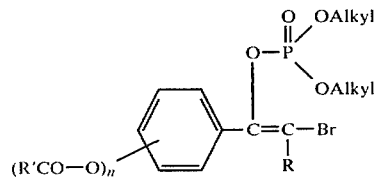

VI

The thus formed phosphate ester crystallizes out in the working up, however, not as a disturbing by-product, but surprisingly remains in solution in the crystallization of the monobromoketone.

Before the addition of the phosphite the hydrogen bromide formed in the bromination should be removed as completely as possible from the reaction medium (for example by passing an inert gas such as nitrogen, air, $CO_2$ or hydrogen through the reaction mixture for 1-3 hours).

Especially with large amounts of ingredients in a given case it is suitable after the bromination, for example by addition of a tertiary amine (for example pyridine, N,N-dimethyl aniline or lower trialkyl amines such as triethyl amine or tributyl amine) to establish a pH range of about 3-6.5 and then first add the acid and the phosphite. If there is still too much HBr present (pH < 3) the yield is reduced and the dibromide is not eliminated entirely; the pH however is not permitted to increase over 6.5 since otherwise a strongly colored and impure bromoketone is obtained which proceeds to form a dark syrup in the drying oven.

The pure monobromoketone of formula III is subsequently reacted with an aminoalkyltheophylline of formula II in the usual manner to form the compound of formula IV

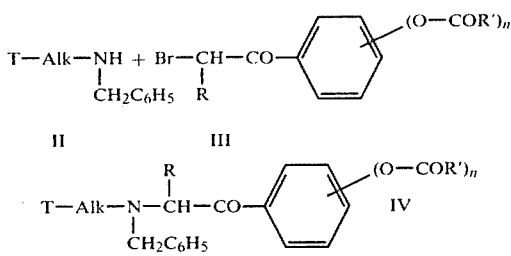

This intermediate product of formula IV is formed in very good yields and can be converted into the pharmacologically interesting end products of formula B in the conventional way by acid deacylation and subsequent catalytic hydrogenation (see, for example, Klingler, Arzneimittelforschung, Volume 27, pages 4-14 (1977)).

Because of the procedure of the invention, it is also possible to carry out the condensation of the bromoketone III with the amine II to the compound IV as well as the deacylation of this compound IV in one reaction step. For this purpose, for example, the reaction mixture which contains the compound IV is filtered, a portion of the solvent drawn off in a vacuum (for example 50-80%), the residue taken up in a $C_1$-$C_4$-alcohol (e.g., methanol, ethanol, isopropanol, propanol, butanol) or in an alcohol-water mixture (mixture of a $C_2$-$C_4$-alcohol and water for example in the weight ratio of 10-6:1, e.g., 10-6 parts of ethanol to 1 of water) and then the mixture acidified with 10-20% alcoholic-aqueous mineral acid (for example, 10% methanolic hydrochloric acid, sulfuric acid) and heated to 50°-100° C.

The superiority of the process of the invention compared to the process described in Arzneimittelforschung, for example, for the already mentioned synthesis of the compound of formula B wherein R is H, Alk is $(CH_2)_3$, n is 2 and the OH groups are in the 3,5-position is demonstrated with the aid of the following figures:

| Industrial Scale (5 kg to 200 kg - ingredients) | | |
|---|---|---|
| | Yields | |
| 3,5-diacetoxyacetophenone | (a) Known Process | (b) Process of the Invention |
| 3,5-diacetoxy-α-bromacetophenone | 80% (contains still 10 to 20% impurities as for example dibromketone) | 85% (pure monobromketone) |

-continued

Industrial Scale (5 kg to 200 kg - ingredients)

| | Yields | |
|---|---|---|
| Condensations product IV | 62% (impure) | 97.5% (pure) |
| Deacetylated condensations product I (Alk: —CH$_2$)$_3$—, R = H, 3,5-dihydroxy) as direct preliminary step of compound B | 71% (impure) | 92% (pure) |
| | Total Yield: 35% | Total Yield: 76% |

Compounds within formula I which can be made according to the invention in addition to those in the specific examples include, for example
7-{4-[2-(3,5-dihydroxyphenyl)- 2-oxo-ethyl-benzyl-amino]-butyl}-theophylline,
7-{2-[2-(3,5-dihydroxyphenyl)-2-oxo-ethyl-benzyl- amino]-ethyl}-theophylline,
7-{1-methyl-3-[2-(3,5-dihydroxyphenyl)-2-oxo-ethyl-benzyl-amino]-propyl}-theophylline,
7-{3-[2-(2,6-dihydroxyphenyl)-2-oxo-ethyl-benzyl-amino]-propyl}-theophylline,
7-{3-[2-(3,5-dihydroxyphenyl)-1-methyl- 2-oxo-ethyl-benzyl-amino]-propyl}-theophylline,
7-{3-[2-(3-hydroxyphenyl)-2-oxo-ethyl-benzyl-amino]-propyl}-theophylline.

The compounds of formula I can be prepared either as the free bases or in the form of a pharmacological salt, e.g., the hydrochloride. Thus the hydrochloride salts can be converted to the free bases in conventional manner, e.g., by neutralization of a methanol solution of the salt with sodium hydroxide, sodium carbonate, etc. In place of forming the hydrochloride salts, there can be formed salts with other acids, e.g., hydrobromic acid, sulfuric acid, p-toluene sulfonic acid, acetic acid, propionic acid, succinic acid, maleic acid, malonic acid, fumaric acid, lactic acid, tartaric acid, citric acid.

As ketones of formula V, there can be used, for example, in addition to the ketones of the specific examples 3,5-diacetoxypropiophenone, p-acetoxypropiophenone, o-acetoxyacetophenone, m-acetoxyacetophenone, 2,6-diacetoxyacetophenone, 2,4-diacetoxyacetophenone, 3,5-dipropionoxyacetophenone, p-propionoxyacetophenone, 3,5-dibutyroxyacetophenone, p-butyroxyacetophenone, 3,5-divaleroxyacetophenone, p-valeroxyacetophenone, 3,5-dicapro-oxyacetophenone.

Examples of additional acids having a p$_K$ of 2-10 are adipic acid, d-alanine, o-aminobenzoic acid, butyric acid, citric acid, formic acid, glutaric acid, glycolic acid, m-hydroxybenzoic acid, lactic acid, maleic acid, octanoic acid, succinic acid, tartaric acid.

Examples of lower trialkyl phosphites in addition to those in the working examples include trimethyl phosphite, dimethyl ethyl phosphite, tripropyl phosphite, triisopropyl phosphite, tributyl phosphite, tri-sec.butyl phosphite, triamyl phosphite, trihexyl phosphite, trioctyl phosphite, tris(2-ethylhexyl) phosphite.

Unless otherwise indicated all parts and percentages are by weight.

The process can comprise, consist essentially of or consist of the steps set forth and the compositions can comprise, consist essentially of or consist of the materials set forth.

DESCRIPTION OF THE PREFERRED EMBODIMENTS

EXAMPLE 1

(a) α-Brom-3,5-diacetoxyacetophenone 8.25 kg of 3,5-diacetoxyacetophenone were dissolved in 40 liters of dichloromethane in a 100 liter glass apparatus. There was allowed to run in under strong stirring and with the passing through of nitrogen a solution of 6.44 kg of dry bromine in 12.5 liters of dichloromethane within 4 hours at about 15° C. For complete removal of the HBr formed nitrogen was led through the solution for one more hour.

Then there were added 0.258 kg of glacial acetic acid and 0.694 kg of triethyl phosphite, stirring carried out at about 20° to 25° C. for 1 hour and subsequently heating carried out at reflux for 15 minutes. The solvent was distilled off under reduced pressure. The residue was dissolved in 28 liters of isopropanol and the solution obtained cooled at about 10° C. with stirring. After standing for three hours at this temperature, the mixture was centrifuged and washed with some cold isopropanol. Drying was carried out at 40° C. in a vacuum.

Yield: 9.3 grams=85% of Theory; M.P. 70° C.;
DC (solvent:chloroform: 1 HF, side spots: 0 to 1.

(b) 7-{3-[2-(3,5-Diacetoxyphenyl)-2-oxo-ethyl-benzylamino]-propyl}-theophylline-hydrochloride A mixture of 6.9 kg α-brom-3,5-diacetoxyaceto-phenone, 15.05 kg of 7-(3-benzylamino-propyl)-theophylline and 57 liters of toluene were boiled at reflux for 90 minutes with stirring and the passing through of nitrogen. The mixture was allowed to cool to 50° C., the precipitated HBr-salt of the excess benzylaminopropyl-theophylline centrifuged off, the mixture washed with about 5 liters of toluene and from the filtrate about 80% of the toluene present distilled off. Subsequently the residue was dissolved in 44 liters of isopropanol and 7 liters of water, the solution obtained cooled to 15°-20° C. and acidified with an isopropanolic-aqueous hydrochloric acid (pH 2-3). After standing for 3 hours under water cooling, the mixture was centrifuged, washed with cold isopropanol and the yield determined by means of a sample drying.

Yield: 12.8 kg=97.5% of Theory; M.P. 115° C.

(c) 7-{3-[2-(3,5-Dihydroxyphenyl)-2-oxo-ethyl-benzyl-amino]-propyl}-theophylline-hydrochloride The wet product of step (b) containing 12.8 kg of diacetyl compound was added to 25.6 liters of methanol and 12.8 liters of 10% hydrochloric acid. The mixture was boiled for one hour at reflux, treated with some activated carbon and kieselguhr, filtered and allowed to cool. On the next day it was centrifuged, washed with water and dried.

Yield: 10.1 kg=92% of Theory; M.P. 215° C.; DC: 1 HF, no side spots.

EXAMPLE 2

(a) α-Brom-4-acetoxyacetophenone

There was added to a solution of 17.8 kg of p-acetoxy acetophenone in 90 liters of dry chloroform a solution of 9.2 kg of bromine in 20 liters of chloroform with stirring in a nitrogen stream within 3 hours. After the HBr formed was completely driven out by nitrogen, there were added 0.37 kg of glacial acetic acid and 1 kg of triethyl phosphite and stirring continued for 1 hour at 20° C. and for another ½ hour at reflux temperature. Then it was evaporated in a vacuum and the residue dissolved in isopropanol.

After 8 hours the mixture was filtered with suction and dried at 40° C. in a vacuum.

Yield: 20.8 kg=81% of Theory; M.P. 68° C.; DC (solvent:chloroform): 1 HF, no side spots.

(b) 7-{3-[2-(4-Acetoxyphenyl)-2-oxo-ethyl-benzyl-amino]-propyl}-theophylline-hydrochloride There were mixed 7.2 kg of α-brom-4-acetoxyacetophenone with 18.35 kg of 7-(3-benzylamino-propyl)-theophylline and 67 liters of toluene and the mixture boiled for 2 hours at reflux. After cooling to 50° to 60° C., the mixture was filtered with suction an the filtrate evaporated in a vacuum. The residue was dissolved in isopropanol and adjusted to a pH of 2 with concentrated hydrochloric acid. After 5 hours the mixture was filtered with suction and dried.

Yield: 14.1 kg=93.5% of Theory; M.P. 202°-204° C.

(c)

The thus obtained crude product was deacetylated by boiling for 1 hour with hydrochloric acid analogous to Example 1. There was obtained 12.5 kg 7-{3-[2-(4-hydroxyphenyl)-2-oxo-ethyl-benzylamino]-propyl}-theophylline-hydrochloride.

=96% of Theory
M.P. 200°-202° C. (from methanol).

EXAMPLE 3

(Example of a bromination with addition of amine)

There were dropped into a solution of 236 grams of 3,5-diacetoxyacetophenone in 1150 ml of methylene chloride within 1 hour 184 grams of bromine in 230 ml of methylene chloride with stirring in a stream of nitrogen. Stirring was continued for one hour under nitrogen and there was added triethyl amine until a pH of 5-6 was reached (about 17 grams). Subsequently there were added 7.4 grams of glacial acetic acid and 19.8 grams of triethyl phosphite and stirring carried out for 1 hour at 20° C. and then for 20 minutes at 40° C. The solvent was distilled off in a vacuum, the residue dissolved in 125 ml of isopropanol, filtered and allowed to stand one day in the refrigerator. The α-brom-3,5-diacetoxyacetophenone was filtered off with suction, washed with ice cold isopropanol and dried at 40° C. in a vacuum.

Yield: 274 grams=87% of Theory; M.P. 68°-69° C.

The entire disclosure of British priority application No. 27707/78 is hereby incorporated by reference.

What is claimed is:

1. A process of preparing a theophylline derivative of the formula

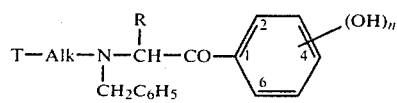

where T is the theophyllinyl-(7)-group, Alk is $(CH_2)_3$, R is hydrogen or a methyl group, n is 1 or 2 with the proviso that two hydroxy groups of the phenyl ring cannot be in the 3,4-positions comprising reacting an aminoalkyltheophylline of the formula

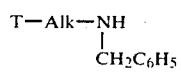

with a bromoketone of the formula

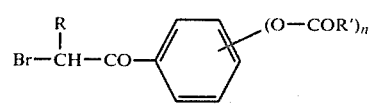

where R' is a lower alkyl group with the proviso that the two —OCOR' groups of the phenyl ring cannot be in the 3,4-positions to form an intermediate compound of the formula

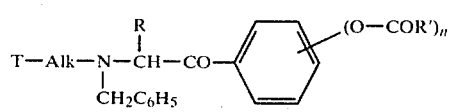

and subsequently hydrolytically splitting off the R'CO protective group, said bromoketone of formula III having been produced free of dibromide by bromination of a ketone of the formula

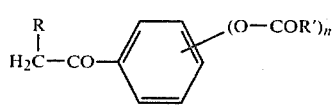

with bromine following by treatment with a lower trialkyl phosphite.

2. A process according to claim 1 wherein the treatment with the phosphite is carried out at a pH of 3 to 6.5.

3. A process according to claim 2 wherein the hydrogen bromide formed is removed from bromoketone prior to the treatment with the phosphite.

4. A process according to claim 3 wherein the phosphite treatment is carried out in the presence of an acid having a $p_K$ of 2-10.

5. A process according to claim 4 wherein the acid has a $p_K$ of 2-5.

6. A process according to claim 5 wherein the acid is acetic acid.

7. A process according to claim 3 wherein n is 2 and the —O—COR' groups are in the 3 and 5 positions.

8. A process according to claim 3 wherein n is 1 and the —O—COR' group is in the 4 position.

9. A process of preparing a pure bromoketone of the formula

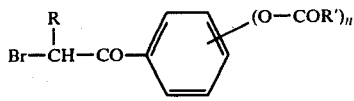

where R' is a lower alkyl group, R is hydrogen or methyl, n is 1 or 2 comprising bromination of a ketone of the formula

with bromine followed by treatment with a lower trialkyl phosphite.

10. A process according to claim 9 wherein the phosphite treatment is carried out in the presence of an acid having $p_K$ of 2–10.

11. A process according to claim 10 wherein the acid has a $p_K$ of 2–5.

12. A process according to claim 11 wherein the acid is acetic acid.

13. A process according to claim 10 wherein the treatment with the phosphite is carried out at a pH of 3 to 6.5.

14. A process according to claim 13 wherein the acid has a $p_K$ of 2–5.

15. A process according to claim 9 wherein the treatment with the phosphite is carried out at a pH of 3 to 6.5.

16. A process according to claim 9 wherein the bromination is carried out with an excess of bromine and the phosphite is used in an amount approximately equivalent to the amount of excess bromine.

17. A process according to claim 16 wherein there is used 5 to 30% excess bromine.

18. A process according to claim 17 wherein substantially all of the hydrogen bromide formed in the bromination reaction is removed prior to addition of the phosphite.

19. A process according to claim 18 wherein the treatment with the phosphite is carried out at a pH of 3 to 6.5.

20. A process according to claim 1 where R is hydrogen, n is 2 and the —O—COR' groups are in the 3 and 5 positions.

21. A process according to claim 1 where R is hydrogen, n is 1 and the —O—COR' group is in the 4 position.

* * * * *